United States Patent
Malandain

(10) Patent No.: US 9,358,134 B2
(45) Date of Patent: Jun. 7, 2016

(54) METHOD OF INSERTING AN INTERBODY FUSION DEVICE

(71) Applicant: SPINE WAVE, INC., Shelton, CT (US)

(72) Inventor: Hugues Malandain, Easton, CT (US)

(73) Assignee: SPINE WAVE, INC., Shelton, CT (US)

( * ) Notice: Subject to any disclaimer, the term of this patent is extended or adjusted under 35 U.S.C. 154(b) by 0 days.

(21) Appl. No.: 14/507,958

(22) Filed: Oct. 7, 2014

(65) Prior Publication Data

US 2015/0025640 A1  Jan. 22, 2015

Related U.S. Application Data

(62) Division of application No. 13/796,160, filed on Mar. 12, 2013, now Pat. No. 8,864,830.

(51) Int. Cl.
 *A61F 2/46* (2006.01)
 *A61F 2/44* (2006.01)
 *A61F 2/30* (2006.01)

(52) U.S. Cl.
 CPC ............... *A61F 2/4611* (2013.01); *A61F 2/442* (2013.01); *A61F 2/447* (2013.01); *A61F 2002/30784* (2013.01); *A61F 2002/30904* (2013.01); *A61F 2002/4475* (2013.01)

(58) Field of Classification Search
 CPC .............. A61B 2017/0256; A61F 2/4611
 USPC ............... 606/90, 99, 86 A; 623/17.11–17.16
 See application file for complete search history.

(56) References Cited

U.S. PATENT DOCUMENTS

| | | |
|---|---|---|
| 3,486,505 A | 12/1969 | Morrison |
| 4,501,269 A | 2/1985 | Bagby |
| 4,863,476 A | 9/1989 | Shepperd |
| 5,431,658 A | 7/1995 | Moskovich |
| 5,554,191 A | 9/1996 | Lahille et al. |
| 5,571,109 A | 11/1996 | Bertagnoli |
| 5,681,265 A | 10/1997 | Maeda et al. |
| 5,766,252 A | 6/1998 | Henry et al. |
| 6,004,326 A * | 12/1999 | Castro ............... A61B 17/025 606/99 |
| 6,059,829 A * | 5/2000 | Schlapfer ............ A61F 2/447 606/247 |
| 6,102,950 A | 8/2000 | Vaccaro |
| 6,113,602 A | 9/2000 | Sand |
| 6,200,322 B1 | 3/2001 | Branch et al. |
| 6,562,074 B2 | 5/2003 | Gerbec et al. |
| 6,814,737 B2 | 11/2004 | Cauthen |
| 6,887,248 B2 | 5/2005 | McKinley et al. |
| 7,204,851 B2 | 4/2007 | Trieu et al. |
| 7,235,082 B2 * | 6/2007 | Bartish ............... A61F 2/4465 606/99 |
| 7,320,688 B2 | 1/2008 | Foley et al. |

(Continued)

FOREIGN PATENT DOCUMENTS

| | | |
|---|---|---|
| EP | 1099429 A1 | 5/2001 |
| FR | 2719763 A1 | 11/1995 |

(Continued)

*Primary Examiner* — Zade Coley

(74) *Attorney, Agent, or Firm* — Hoffmann & Baron, LLP

(57) ABSTRACT

An apparatus for use in spinal interbody fusion comprises, in combination, a spinal interbody fusion implant and an inserter releasably attached thereto. The implant comprises a hollow interior through which the inserter extends, the inserter having a tapered distal tip projecting exteriorly beyond the distal end of the implant to initially distract opposing tissue surfaces and to facilitate insertion of the implant into the intradiscal space between the vertebral bodies.

5 Claims, 7 Drawing Sheets

(56) References Cited

U.S. PATENT DOCUMENTS

| | | | |
|---|---|---|---|
| 7,485,120 B2 | 2/2009 | Ray | |
| 7,625,379 B2 | 12/2009 | Puno et al. | |
| 7,749,253 B2 * | 7/2010 | Zucherman | A61B 17/025 606/100 |
| 7,857,818 B2 | 12/2010 | Trieu et al. | |
| 7,922,729 B2 * | 4/2011 | Michelson | A61F 2/44 606/99 |
| 8,016,829 B2 | 9/2011 | Mahoney et al. | |
| 8,025,655 B2 | 9/2011 | Kugler et al. | |
| 8,025,665 B2 * | 9/2011 | Lim | A61B 17/025 606/105 |
| 8,038,715 B2 | 10/2011 | Kim et al. | |
| 8,043,344 B2 | 10/2011 | Evans et al. | |
| 8,066,710 B2 | 11/2011 | Estes et al. | |
| 8,114,088 B2 | 2/2012 | Miller | |
| 8,216,313 B2 | 7/2012 | Moore | |
| 8,226,691 B2 | 7/2012 | McDonnell | |
| 8,267,939 B2 * | 9/2012 | Cipoletti | A61F 2/447 606/99 |
| 8,430,930 B2 | 4/2013 | Hunt | |
| 8,828,062 B2 * | 9/2014 | McCormack | A61B 17/025 606/247 |
| 8,932,302 B2 | 1/2015 | Jimenez et al. | |
| 2001/0012942 A1 | 8/2001 | Estes et al. | |
| 2002/0055745 A1 | 5/2002 | McKinley et al. | |
| 2002/0116009 A1 | 8/2002 | Fraser et al. | |
| 2003/0023245 A1 * | 1/2003 | Ralph | A61F 2/442 606/99 |
| 2003/0135220 A1 | 7/2003 | Cauthen | |
| 2003/0135275 A1 * | 7/2003 | Garcia | A61B 17/1671 623/17.11 |
| 2004/0133280 A1 * | 7/2004 | Trieu | A61F 2/44 623/17.16 |
| 2005/0038431 A1 * | 2/2005 | Bartish | A61F 2/4465 606/86 A |
| 2007/0043376 A1 | 2/2007 | Leatherbury et al. | |
| 2007/0129730 A1 * | 6/2007 | Woods | A61F 2/4425 606/99 |
| 2007/0142841 A1 * | 6/2007 | Reitzig | A61F 2/4611 606/90 |
| 2007/0149978 A1 * | 6/2007 | Shezifi | A61B 17/025 606/90 |
| 2007/0208347 A1 * | 9/2007 | Zucherman | A61B 17/025 606/249 |
| 2007/0293949 A1 * | 12/2007 | Salerni | A61F 2/4455 623/17.16 |
| 2008/0015701 A1 | 1/2008 | Garcia et al. | |
| 2008/0154377 A1 | 6/2008 | Voellmicke | |
| 2008/0275455 A1 | 11/2008 | Berry et al. | |
| 2008/0287957 A1 | 11/2008 | Hester et al. | |
| 2009/0048604 A1 | 2/2009 | Milz et al. | |
| 2009/0228110 A1 * | 9/2009 | McClintock | A61F 2/4455 623/17.16 |
| 2009/0281551 A1 * | 11/2009 | Frey | A61B 17/025 606/99 |
| 2010/0023013 A1 * | 1/2010 | Flickinger | A61B 17/025 606/79 |
| 2011/0184522 A1 * | 7/2011 | Melkent | A61F 2/4611 623/17.16 |

FOREIGN PATENT DOCUMENTS

| | | | | |
|---|---|---|---|---|
| WO | WO 2007008333 A2 * | 1/2007 | ......... | A61B 17/3478 |
| WO | 2012009152 A1 | 1/2012 | | |

* cited by examiner

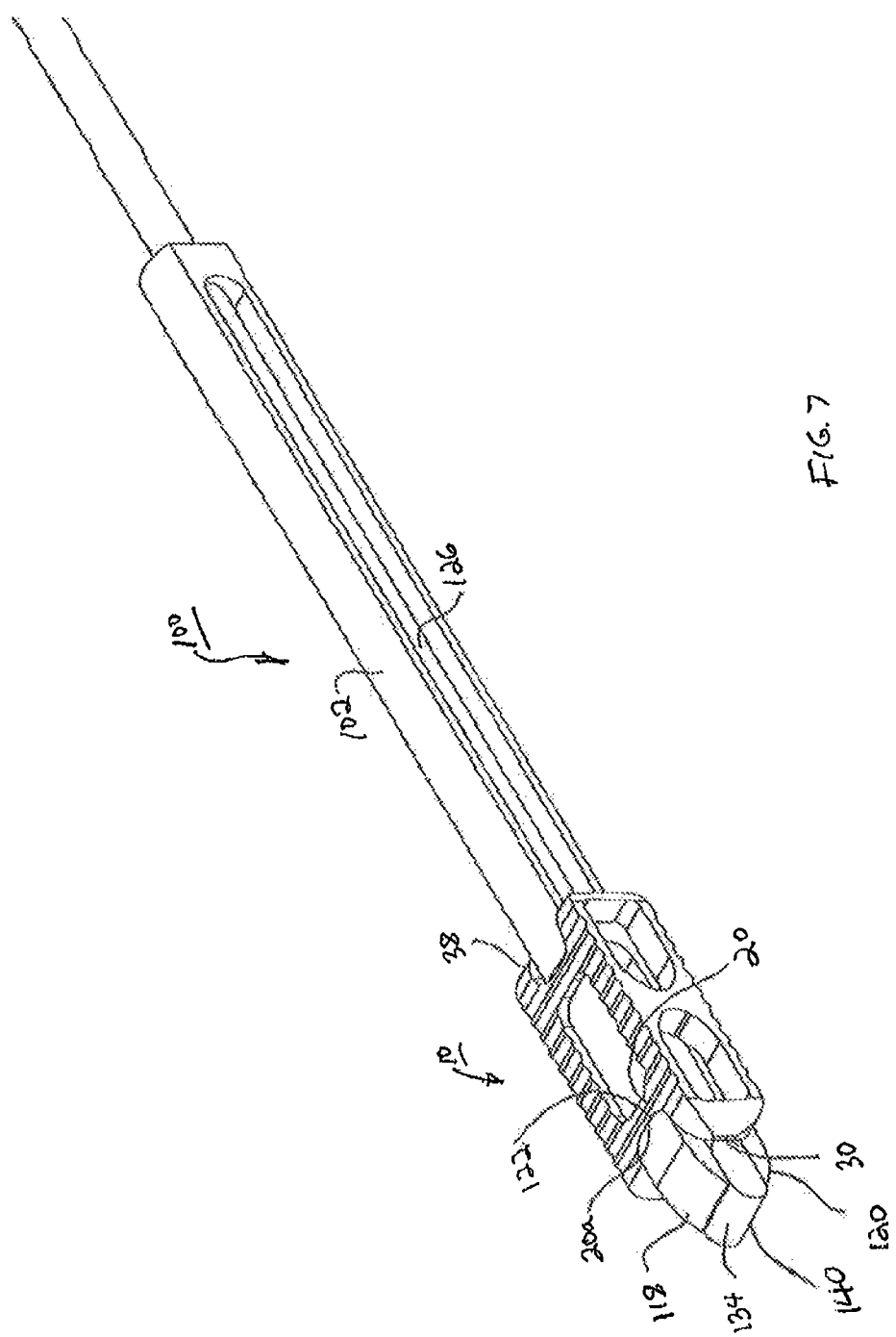

METHOD OF INSERTING AN INTERBODY FUSION DEVICE

CROSS-REFERENCE TO RELATED APPLICATION

This application is a divisional application of U.S. application Ser. No. 13/796,160, filed Mar. 12, 2013, now U.S. Pat. No. 8,864,830, the entire contents of which are incorporated by reference herein.

FIELD OF THE INVENTION

The subject invention relates generally to the field of spinal implants and more particularly to an insertion instrument and methods for inserting a spinal implant between opposing spinal tissue surfaces.

BACKGROUND OF THE INVENTION

Spinal implants such as interbody fusion devices are used to treat degenerative disc disease and other damages or defects in the spinal disc between adjacent vertebrae. The disc may be herniated or suffering from a variety of degenerative conditions, such that the anatomical function of the spinal disc is disrupted. Most prevalent surgical treatment for these conditions is to fuse the two vertebrae surrounding the affected disc. In most cases, the entire disc will be removed, except for a portion of the annulus, by way of a discectomy procedure. A spinal fusion device is then introduced into the intradiscal space and suitable bone graft or bone substitute material is placed substantially in and/or adjacent the device in order to promote fusion between two adjacent vertebrae.

There are a variety of implants for spinal fusion in current use, some of which are expandable and others of fixed dimension. In order to accommodate the spinal anatomy and promote arthrodesis, an interbody fusion device preferably has optimized contact with adjacent endplates. This is commonly achieved by ensuring that the interface between the device and the bony endplates of opposing vertebral bodies includes a surface area as large as practicable. In turn, this means that the distal tip of the device is often restricted to have a blunt nose, making it challenging for the surgeon to insert the device in the intradiscal space. A common approach to surmounting this challenge is to form the distal tip of the implant with a bullet-type nose. Such an implant is described, for example, in U.S. Pat. No. 5,766,252 issued to Henry et al. on Jun. 16, 1998. The potential disadvantage to such design is that while the implant is easier to insert and impact into the intradiscal space, it offers less interface area between the implant and the endplates since the bullet nose portion of the device does not contact the endplates. In addition, when such implants are inserted posteriorly, the bullet nose is situated ultimately in the anterior portion of the intradiscal space and disadvantageously occupies space where bone graft is preferably placed to improve arthrodesis.

Accordingly, there is a need to develop an interbody fusion device and insertion technique that provides the advantages of the bullet nose devices while optimizing the contact area between the device and the opposing vertebral endplates.

SUMMARY OF THE INVENTION

It is an object of the invention to provide an improved apparatus for use in implantation of a spinal implant between two opposing tissue surfaces a spine in spinal surgery. In a particular arrangement, the apparatus comprises, in combination, a spinal implant that has a body including a distal end, a proximal and an engagement surface, and an inserter comprising a distal end and a proximal end, the inserter being releasably attached to the implant. The proximal end of the implant extends exteriorly outside the proximal end of the implant body. The distal end of the inserter includes a resilient latching surface in releasable engagement with the engagement surface of said implant body and has a distal tip projecting exteriorly beyond the distal end of the implant body, the distal tip comprising a tapered surface.

It is a further object of the invention to provide an improved apparatus for use in implantation of an interbody fusion device into the intradiscal space between two opposing vertebral bodies of a spine.

DESCRIPTION OF THE FIGURES

FIG. 7 is a top perspective view of the implant and inserter of FIG. 6.

DESCRIPTION OF THE EMBODIMENTS

Figure 1:
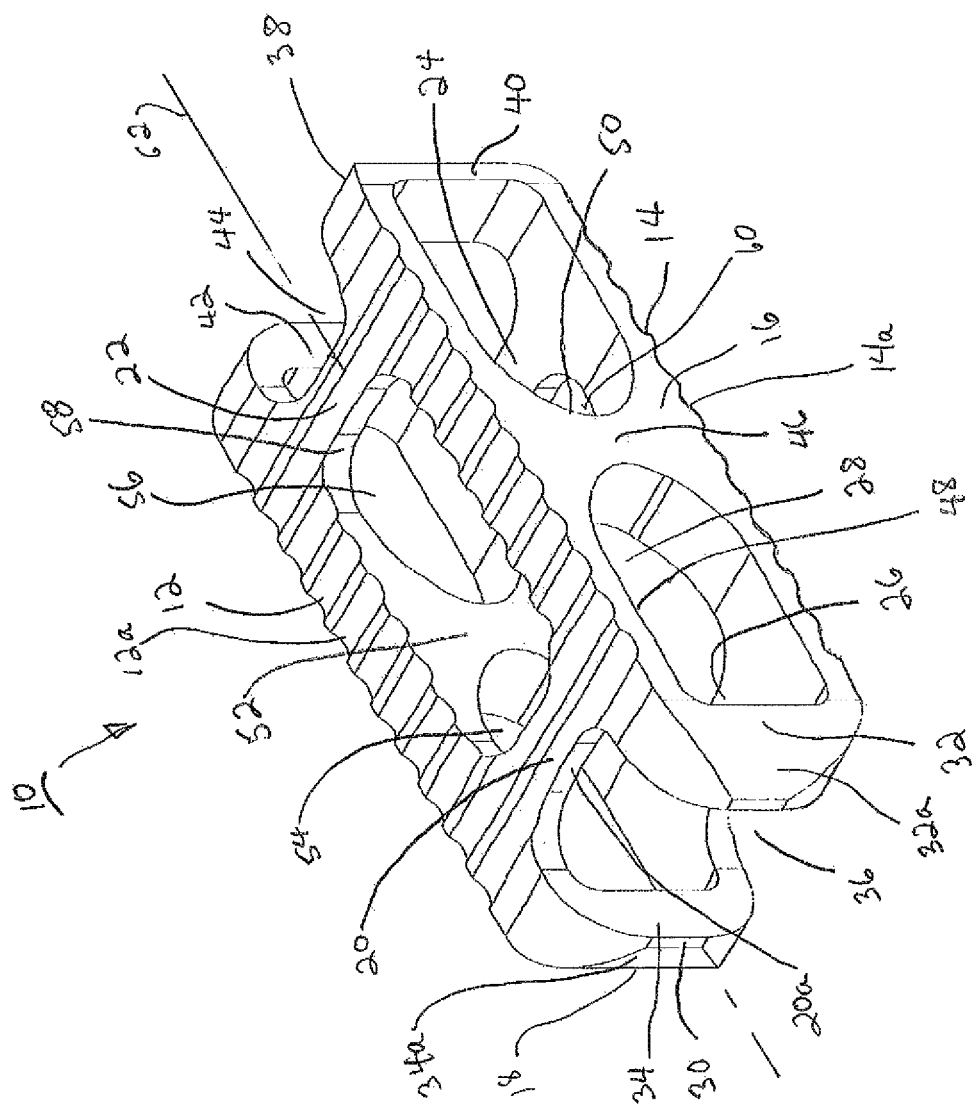
FIG. 1 is a front perspective view of a hollow fixed dimension interbody fusion implant in accordance with an embodiment of the present invention.

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, a spinal implant 10 is shown that in one particular arrangement includes a cage-like body, having a hollow interior. In such arrangement, implant 10 is a monolithic, non-expandable device that may be used in an interosseous space and that, in particular, is suitable as a spinal interbody fusion implant. As such, the interbody fusion implant 10 includes an upper bone contact surface 12 and a spaced opposing lower bone contact surface 14 that are configured to contact endplates of opposing vertebral bodies in a spine defining a volume between vertebrae in the intradiscal space after a natural disc has been removed in preparation for the implantation of the implant. Implant 10 includes opposing spaced apart side surfaces 16 and 18 that are interconnected to each other by a plurality of laterally extending cross members 20, 22, 24 and 26. The forward end surfaces 20a of top cross member 20 and of bottom cross member 26a (not shown) provide respective engagement surfaces for engagement with an insert or instrument, and will be described. The upper and lower bone contact surfaces 12, 14 and the side surfaces 16, 18 define a hollow interior 28 of implant 10.

The upper and lower bone contact surfaces 12, 14 are joined at the distal end 30 of implant 10 by a pair of rigid arms 32 and 34 defining an opening 36 at the distal end 30. The upper and lower bone contact surfaces 12, 14 are joined at the proximal end 38 by a pair of rigid arms 40 and 42 defining an opening 44 at the proximal end 38. Side surface 16 comprises a generally centrally located load bearing column 46 that defines with arms 32 and 40 a pair of windows 48 and 50 respectively extending therethrough and communicating with the hollow interior 28. Side surface 18 comprises a generally centrally located load bearing column 52 that defines with arms 34 and 42 pair of windows 54 and 56 respectively extending therethrough and communicating with the hollow interior 28.

The upper and lower bone contact surfaces 12, 14 include upper and lower openings 58 and 60 respectively allowing bone graft or other osteogenic materials to flow into the hollow interior 28 of the implant 10 to pass through to adjacent vertebral body endplates thereby aiding in the fusion of the implant thereto. Upper opening 58 is disposed between crossmembers 20 and 22 and lower opening 60 is disposed between crossmembers 24 and 26. The distal end 30 of implant 10 defined by the arms 32 and 34 defines a generally blunt leading end while the proximal end 38 defined by arms 40 and 42 similarly defines a generally blunt trailing end. The generally blunt ends allow the upper and lower bone contact surfaces 12, 14 to have a length along and generally parallel to axis 62 optimized for maximum contact with endplates of opposing vertebral bodies. The exterior side surfaces 32a and 34a of distal arms 32 and 34 may, however, be curved to provide a relatively smooth surface for entry of the implant 10 into the intradiscal space.

The bone contact surfaces 12, 14 include serrations 12a and 14a serving a bone anchoring function. These functional anchors may assist in holding a bone contact surface on the implant 10 in position during implantation or may hold the implant in position after implantation. Other forms of functional bone anchoring components, e.g., fins, spikes, hooks, etc., may be substituted as desired. In addition to limiting movement of the implant along (or parallel to) the vertebral body endplates these fixation features, in some instances, provide for permanent ingrowth between bone and implant. The upper and lower bone contact surfaces 12, 14 each have a width between the exterior surfaces of side surfaces 16, 18, generally perpendicular to the longitudinal axis 62 of the implant 10 and a length along and generally parallel to the axis 62 of the implant 10 between the exterior surfaces of distal end 30 and proximal end 38.

Figure 2:
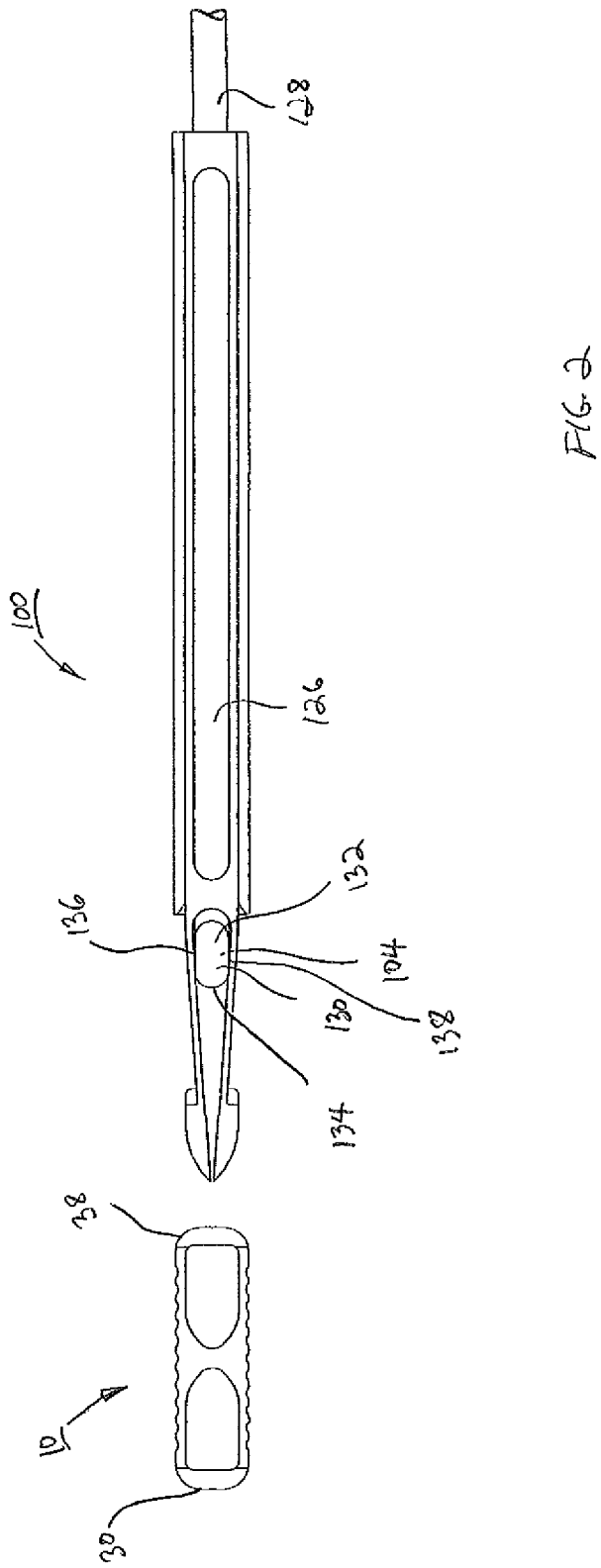
FIG. 2 is side elevation view of the implant of FIG. 1 and an inserter of the present invention.
Figure 3:
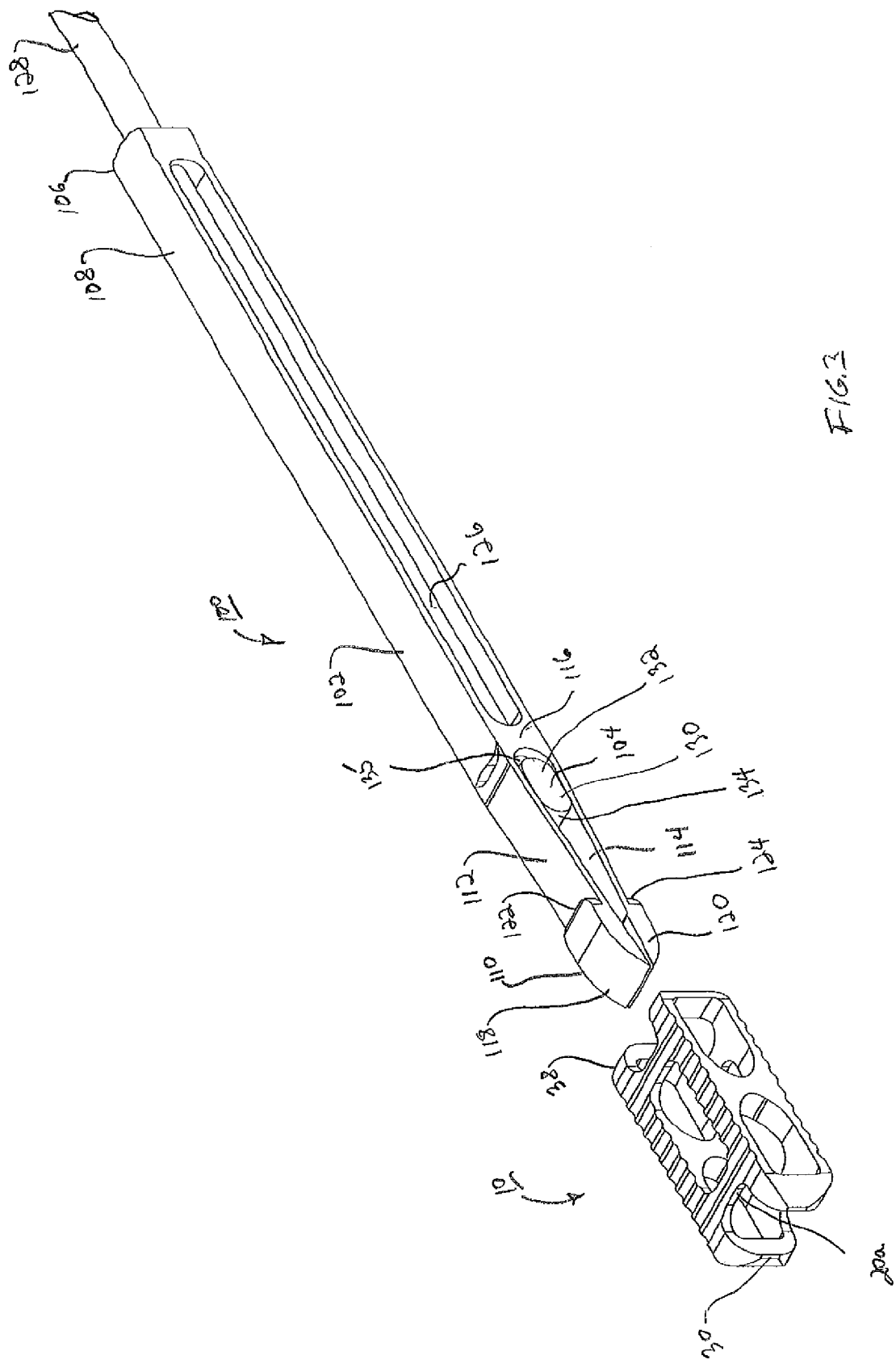
FIG. 3 is a top perspective view of the implant and inserter of FIG. 1.
Figure 4:
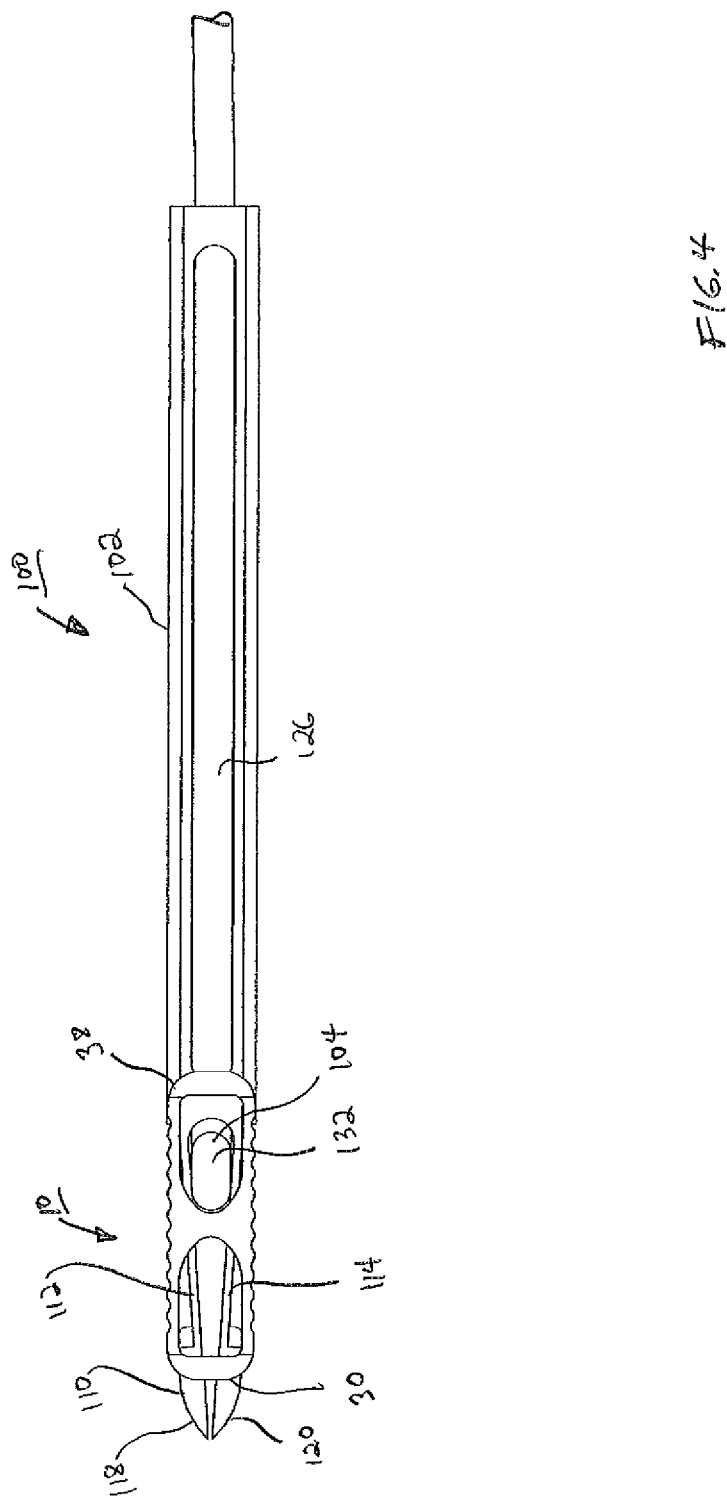
FIG. 4 is a side elevation view of the implant and inserter of FIG. 1 with the implant loaded onto the inserter.
Figure 5:
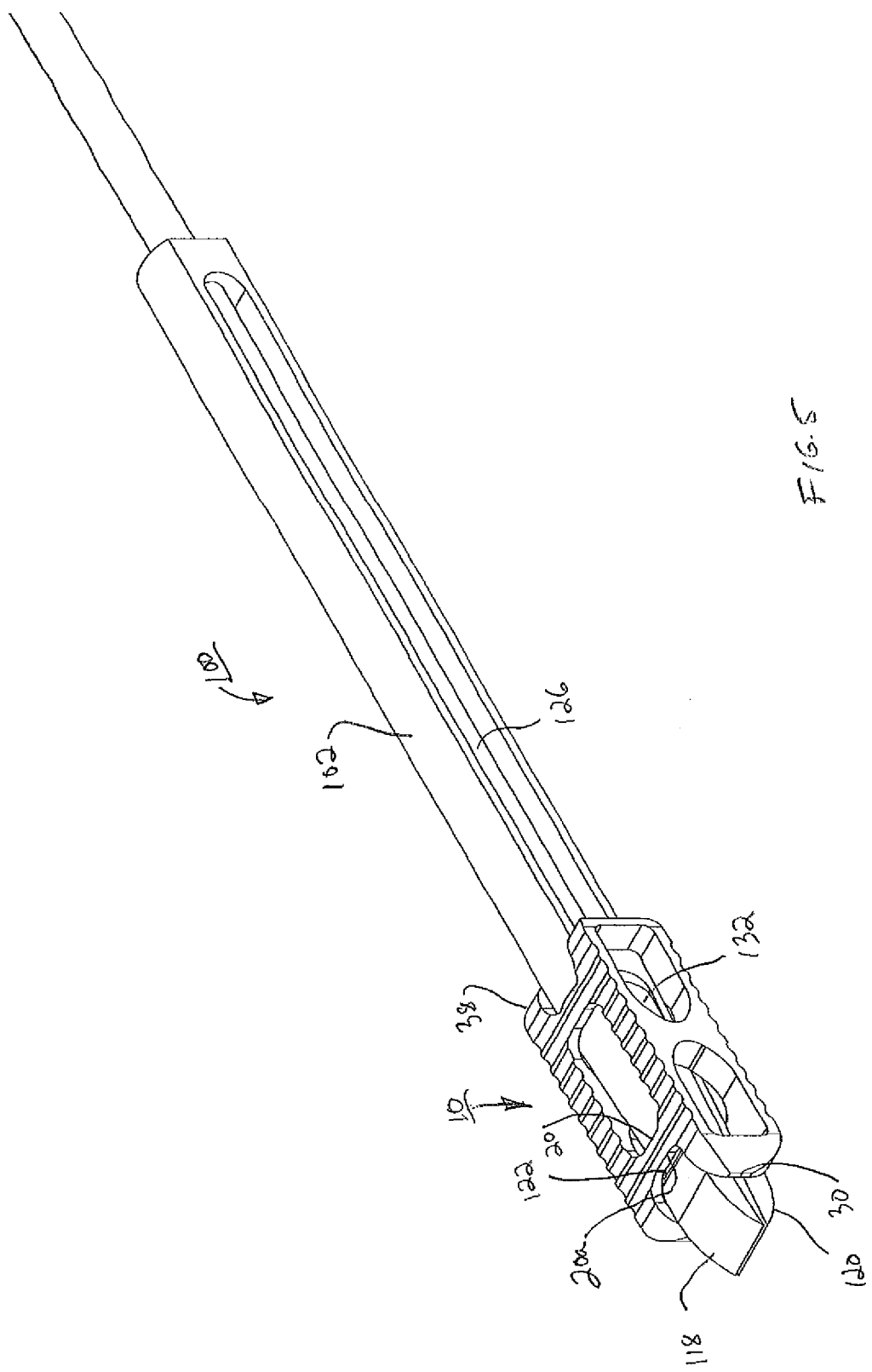
FIG. 5 is a top perspective view of the implant and inserter of FIG. 4.

Turning now to FIGS. 2-3, the details of an instrument for inserting implant 10 into the intradiscal space between the endplates of opposing vertebral bodies are described. Inserter 100 comprises an implant holder 102 and an expander 104 that is received within and translatability supported by holder 102. Holder 102 comprises at its proximal end 106 a handle 108 of size and configuration for grasping by a surgeon and of extent to extend outwardly of the surgical site of a patient. The distal end 110 of holder 102 comprises a pair of flexible arms 112 and 114 that are supported for cantilevered, flexible movement by a fulcrum 116. Each of the arms 112, 114 terminates in a tip portion 118 and 120, respectively, each tip portion 118, 120 being freely movable and having a tapered exterior surface that is preferably curved. Holder 102 is formed of a material such as titanium, stainless steel or other ferrous materials with suitable spring properties that enable arms to flex and the tip portions 118, 120 to be normally biased toward and adjacent each other. Where the inserter 100 is optionally disposable it may include a hybrid of materials, including ferrous materials for the expander 104 and non-ferrous materials for the holder 102. The proximal facing portions of each tip portion 118, 120 defines a latching surface 122 and 124 for releasable engagement with the engagement surfaces 20a and 26a on implant 10, as will be described.

Expander 104 comprises an elongate body 126 having a proximal end 128 and a distal end 130 as shown in FIGS. 2-3. Expander 104 includes at distal end 130 an enlarged distal portion 132 of size and configuration for disposition between the tip portions 118, 120. Distal portion 132 includes a forward facing tapered end extent 134 that is preferably curved and top and bottom generally flat surfaces 136 and 138. Fulcrum 116 of holder 102 has a generally centrally located opening 135 through which distal portion 132 is introduced between flexible arms 112, 114. The holder body 126 is rotated to place the flat portions 136, 138 in generally facing relation to respective flexible arm 112, 114, effectively captivating expander 104 in holder 102.

Turning now to FIGS. 4-7 the manner of joining the implant 10 and inserter 100 in combination is described. As initially shown in FIGS. 4-5, implant 10 is loaded on inserter 100 by the insertion of the distal end 110 of the inserter 100 with expander 104 contained therein into and through the opening 44 at the proximal end 38 of implant 10. Insertion of inserter 100 is continued through the hollow interior 28 of implant 10 until the tip portions 118, 120 extend beyond the cross members 20, 22 and exteriorly beyond the distal end 30 of implant 10.

Figure 6:
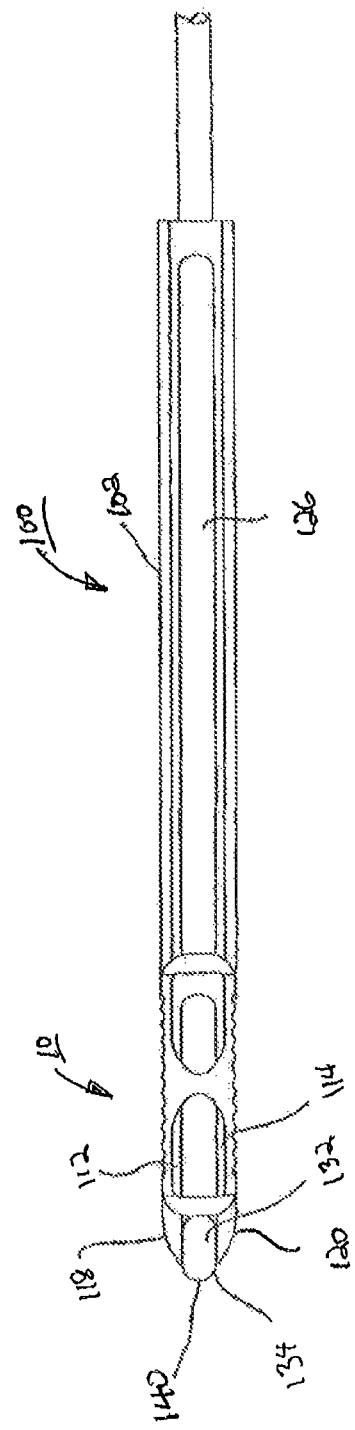
FIG. 6 is a side view of the implant and inserter of FIG. 4 with the implant fully attached to the inserter.

The expander 104 is advanced further distally as illustrated in FIGS. 6-7 such that the enlarged portion 132 engages the flexible arms 112, 114 and resiliently moves the arms 112, 114 away from their initial introduction position to a second latching position whereby the enlarged portion 132 is disposed between and outwardly expands the tip portions 118, 120. In this second latching position, latching surfaces 122, 124 are moved into releasable engagement with engagement surfaces 20a and 26a on respective crossmembers 20 and 26. In this position, the tapered end extent 134 of expander 104 is adjacent to and preferably slightly distally outwardly of the distal ends of tip portions 118, 120 as shown in FIGS. 6-7. Together, the tip portions 118, 120 and end extent 134 define a tapered, distal tip 140. It should be appreciated that the tapered exterior surfaces of tip portions 118, 120 as well as the tapered exterior surface of end extent 134 of expander 104 that define distal tip 140 may be curved in a manner to define a bullet nose configuration. In addition, the tapered surfaces of tip portions 118, 120 and the end extent 134 may also be defined by a flat wedge configuration.

In the stage shown in FIGS. 6-7 the implant 10 with inserter 100 attached thereto is inserted between the tissue surfaces of the endplates of opposing vertebral bodies after suitable removal of disc material with the tapered distal tip 140 providing an initial distraction therebetween. The generally blunt distal and proximal ends 30, 38 respectively of implant 10 allow optimization of implant length for maximum contact area between implant 10 and the opposing vertebral bodies endplates. The compression on implant 10 provided by the ligaments surrounding vertebral bodies on the serrations 12a and 14a will serve to anchor the implant 10 in position.

To remove the inserter 100 from the implant 10 the expander 104 is pulled proximally to move the enlarged portion 132 from a position between tip portions 118, 120 toward the fulcrum 116, allowing the flexible arms to move under their natural bias toward each other and thereby separating the latching surfaces 122, 124 from the engagement surfaces 20a and 26a on implant 10. With the inserter 100 disconnected from implant 10, the inserter 100 may be freely moved proximally to fully remove the inserter 100 from implant 10, which remains anchored in the intradiscal space.

After implantation all or a portion of the interior 28 or periphery of the implant 10 may be filled with a suitable osteogenic material or therapeutic composition. Such materials are more fully disclosed in commonly assigned International Publication Number WO 2012/009152 A1, entitled "A Plastically Deformable Inter-Osseous Device", published on Jan. 19, 2012, and filed in the name of Hugues Malandain, the entire contents of which are incorporated by reference herein.

Suitable biocompatible metallic materials for implant 10 include pure titanium, tantalum, cobalt-chromium alloys, titanium alloys (e.g., nickel titanium alloys and tungsten titanium alloys), and stainless steel alloys. Suitable polymeric materials for implant 10 include members of the polyaryletherketone (PAEK) family, e.g., polyetheretherketone (PEEK), carbon-reinforced PEEK, polyetherketoneketone (PEKK); polysulfone; polyetherimide; polyimide; ultra-high molecular weight polyethylene (UHMWPE); or cross-linked UHMWPE. Ceramic materials such as aluminum oxide or alumina, zirconium oxide or zirconia, compact of particulate diamond, or pyrolytic carbon may be included in such polymers.

The implant 10 may be implanted using the insertion instrument 100 described herein in a variety of approaches, such as, anterior, posterior, lateral and posterolateral. For illustrative purposes, implant 10 may have lengths in the range of 15 mm-55 mm, widths in the range of 5 mm-25 mm, and heights in the range of 6 mm-20 mm so as to allow full use in the spine in the cervical through lumbar regions in the aforementioned approaches for fusion treatments.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected. Also, while the illustrated embodiments have been directed particularly to interbody fusion of the spine, the implant and inserter disclosed herein may be used in other spinal applications that require distraction of tissue surfaces, such as, for example, vertebral compression fracture treatments wherein the implant as supported by the inserter may be introduced into a vertebral body between opposing tissue surfaces within the intervertebral space to stabilize the fracture. The implant and inserter may also be used as a stabilizer between tissue surfaces of opposing spinous processes. Modifications in size may be necessary depending upon the body space being distracted.

What is claimed is:

1. A method of inserting a spinal implant between opposing tissue surfaces of a spine, comprising the steps of:
   releasably attaching an inserter to said spinal implant, said spinal implant including a hollow body having a proximal open end, a distal open end and a distal facing engagement surface, such that an expandable distal end of said inserter defines a tapered distal tip that extends exteriorly distally beyond the distal open end of said implant, said distal tip defining a proximal facing latching surface that upon expansion of said expandable distal end is in releasable engagement with said implant engagement surface;
   inserting said implant with said inserter attached thereto between opposing tissue surfaces of said spine with the tapered distal tip of the distal end of said inserter providing an initial distraction of said tissue surfaces; and
   contracting said expandable distal end of said inserter to remove said inserter from said implant.

2. The method of claim 1, wherein said implant with said inserter attached thereto is inserted between opposing tissue surfaces of spinous processes.

3. The method of claim 1, wherein said implant with said inserter attached thereto is inserted into the intervertebral space within a vertebral body between opposing tissue surfaces therewithin.

4. A method of inserting a spinal interbody fusion implant into the intradiscal space between endplates of opposing vertebral bodies of a spine, comprising the steps of:
   releasably attaching an inserter to said spinal implant, said spinal implant including a hollow body having a proximal open end and a distal open end such that an expandable distal end of said inserter defines a tapered distal tip that extends distally beyond the distal open end of said implant, said inserter comprising a holder including a pair of resilient arms normally biased toward each other, each arm including a latching surface and terminating in a tip portion including an exterior tapered surface, said inserter further comprising an expander supported by said holder for movement between said flexible arms in both proximal and distal directions, said expander comprising an end extent at the distal end comprising a tapered surface, wherein said inserter is attached to said implant by introducing said arms into said hollow spinal implant until said tip portions extend beyond the distal end of said implant and then moving said expander distally to move said tip portions on said arms away from each other and to cause said latching surfaces on said tip portions to resiliently releasably engage said implant, with said end extent being moved adjacent the distal ends of said tip portions to define therewith said tapered distal tip;
   inserting said implant with said inserter attached thereto into the intradiscal space between endplates of opposing vertebral bodies of said spine with said tapered distal tip of the distal end of said inserter providing an initial distraction between said vertebral bodies; and
   contracting said expandable distal end of said inserter to remove said inserter from said implant.

5. The method of claim 4, wherein said inserter is removed from said implant by moving said expander proximally thereby allowing said flexible arms to move under normal bias toward each to thereby separate said latching surfaces from said implant, and thereafter withdrawing said inserter from said implant.

* * * * *